(12) United States Patent
Shibata

(10) Patent No.: US 6,804,984 B2
(45) Date of Patent: Oct. 19, 2004

(54) SHEATH LIQUID SUPPLYING APPARATUS, SHEATH LIQUID SUPPLYING METHOD, AND EVALUATING METHOD OF SHEATH LIQUID SUPPLYING CONDITION

(75) Inventor: Masaharu Shibata, Kobe (JP)

(73) Assignee: Sysmex Corporation, Hyogo (JP)

( * ) Notice: Subject to any disclaimer, the term of this patent is extended or adjusted under 35 U.S.C. 154(b) by 23 days.

(21) Appl. No.: 10/336,789

(22) Filed: Jan. 6, 2003

(65) Prior Publication Data

US 2003/0107725 A1 Jun. 12, 2003

Related U.S. Application Data

(63) Continuation of application No. 09/930,967, filed on Aug. 17, 2001.

(30) Foreign Application Priority Data

Aug. 18, 2000 (JP) ........................................ 2000-248689

(51) Int. Cl.[7] .............................................. G01P 21/00
(52) U.S. Cl. .................. 73/1.36; 73/864.21; 73/864.87
(58) Field of Search ................................ 73/1.36, 1.74, 73/61.48, 64.56, 864.13, 864.18, 864.21, 864.22, 864.87; 250/252.1; 422/82

(56) References Cited

U.S. PATENT DOCUMENTS 3,831,618 A * 8/1974 Liston ......................... 137/154
4,111,051 A * 9/1978 Tamm et al. ............. 73/864.12
4,476,734 A * 10/1984 Banks et al. .............. 73/864.16
4,736,732 A * 4/1988 Shimonaka et al. ........ 600/158
5,182,617 A * 1/1993 Yoneyama et al. ......... 356/440
5,215,714 A    6/1993 Okada et al.
5,374,398 A   12/1994 Isami et al.
5,603,700 A    2/1997 Daneshvar
6,365,106 B1 * 4/2002 Nagai .......................... 422/73

FOREIGN PATENT DOCUMENTS

| JP | 8-201267 A | 8/1996 | |
| JP | 10-260129 A1 | 9/1998 | |
| JP | 02001059839 A | 3/2001 | |
| JP | 2001059839 A | * 3/2001 | .......... G01N/30/18 |

* cited by examiner

Primary Examiner—Hezron Williams
Assistant Examiner—Charles D. Garber
(74) Attorney, Agent, or Firm—Birch, Stewart, Kolascg & Birch, LLP

(57) ABSTRACT

A sheath liquid supplying apparatus includes a syringe including a piston and a cylinder slidably accommodating the piston and a stepping motor for causing the piston to slide in the cylinder, wherein the cylinder has an injection/suction hole of a sheath liquid positioned at a distal end thereof and a gas introducing hole positioned at a side wall thereof for introducing gas into the cylinder.

27 Claims, 7 Drawing Sheets

→Time (200ms/div)

→Time (200ms/div)

→Time (20ms/div)

SHEATH LIQUID SUPPLYING APPARATUS, SHEATH LIQUID SUPPLYING METHOD, AND EVALUATING METHOD OF SHEATH LIQUID SUPPLYING CONDITION

CROSS-REFERENCE TO RELATED APPLICATION

This application is a continuation of co-pending Application No. 09/930,967, filed on Aug. 17, 2001, the entire contents of which are hereby incorporated by reference and for which priority is claimed under 35 U.S.C. § 120; and this application claims priority of Application No. 2000-248689 filed in Japan on Aug. 18, 2000 under 35 U.S.C. § 119.

This application is related to Japanese Patent Application No. 2000-248689 filed in Aug. 18, 2000, whose priority is claimed under 35 USC §119, the disclosure of which is incorporated by reference in its entirety.

BACKGROUND OF THE INVENTION

1. Field of the Invention

The present invention relates to a sheath liquid supplying apparatus, a sheath liquid supplying method and an evaluating method of a sheath liquid supplying condition, and more particularly to an apparatus or method for supplying a sheath liquid to a sheath flow cell by using a syringe in a flow cytometer.

2. Description of the Related Arts

A flow cytometer using a so-called sheath flow method has been well-known as an apparatus for analyzing particles such as a cell, blood cell, or the like in a sample. In this method, a sheath liquid is flown around a sample solution (particle-floating solution) elected from a nozzle in a sheath flow cell to form a sheath flow, whereby the sample solution can be converged into a small flow in the sheath flow cell. The converged sample solution is optically measured for analyzing particles in the sample solution. The "sheath flow" means a flow for causing particles in the particle-floating solution (sample solution) pass therethrough in a line with precision by converging the sample solution into a small flow having an outside diameter approximately same as that of the particle at the center portion of the sheath liquid that is flowing through an orifice in a laminar flow state. Analysis of various cells has been performed by using a sample solution obtained by adjusting a sample of blood or urine with a dyeing solution, hemolytic agent or reaction reagent.

The sample solution is supplied to the sheath flow cell by a syringe having high quantity accuracy. The sheath liquid is supplied to the sheath flow cell by using a method of applying a predetermined positive pressure (0.2–1.6 kgf/cm$^2$) to the sheath liquid chamber (referring to Japanese Unexamined Publication No. HEI 10(1998)-260129).

However, the supply of the sheath liquid to the sheath flow cell by using a method of applying the positive pressure to the sheath liquid chamber brings a change in viscosity of the sheath liquid in the case of changing the environmental temperature. This change in viscosity brings a change in flow velocity, thereby giving an adverse influence to the optical measurement.

Accordingly, this method requires a sheath liquid temperature adjusting function for maintaining a constant flow velocity of the sheath liquid, as well as requires an air compressor for applying the positive pressure to the sheath liquid chamber or a regulator for adjusting a pressure. This causes a problem that a pressure-adjusting and sheath liquid supplying apparatus is made complicated.

In case where the sheath liquid is supplied to the sheath flow cell by using a syringe that is driven by a stepping motor, the flow velocity is not affected by a change in the environmental temperature. However, the flow velocity of the sheath liquid changes depending upon a mechanical factor such as a pulse of a torque of the stepping motor, whereby a ripple occurs on the sheath liquid and sample solution in the sheath flow cell. Specifically, the sheath flow is brought into an unstable state. As a result, a ground noise of an optical detecting signal is fluctuated, which gives an adverse effect on the optical measurement.

SUMMARY OF THE INVENTION

The present invention is accomplished in view of the above circumstances, and aims to provide a sheath liquid supplying apparatus, a sheath liquid supplying method, a flow cytometer including said apparatus, and an evaluating method of a sheath liquid supplying condition wherein a sheath liquid is supplied by using a syringe that is driven by a driving motor. This construction provides that the flow velocity is not affected by an environmental temperature, and prevents a fluctuation in the flow velocity of the sheath liquid due to a mechanical factor such as a pulse of a torque of a stepping motor as well as prevents a fluctuation in a ground noise of an optical detecting signal brought with the fluctuation in the flow velocity.

DESCRIPTION OF THE PREFERRED EMBODIMENT

The present invention will be explained in detail with reference to the drawings. The present invention is not limited to the following explanation.

Construction of a Sheath Liquid Supplying Apparatus

Figure 1:
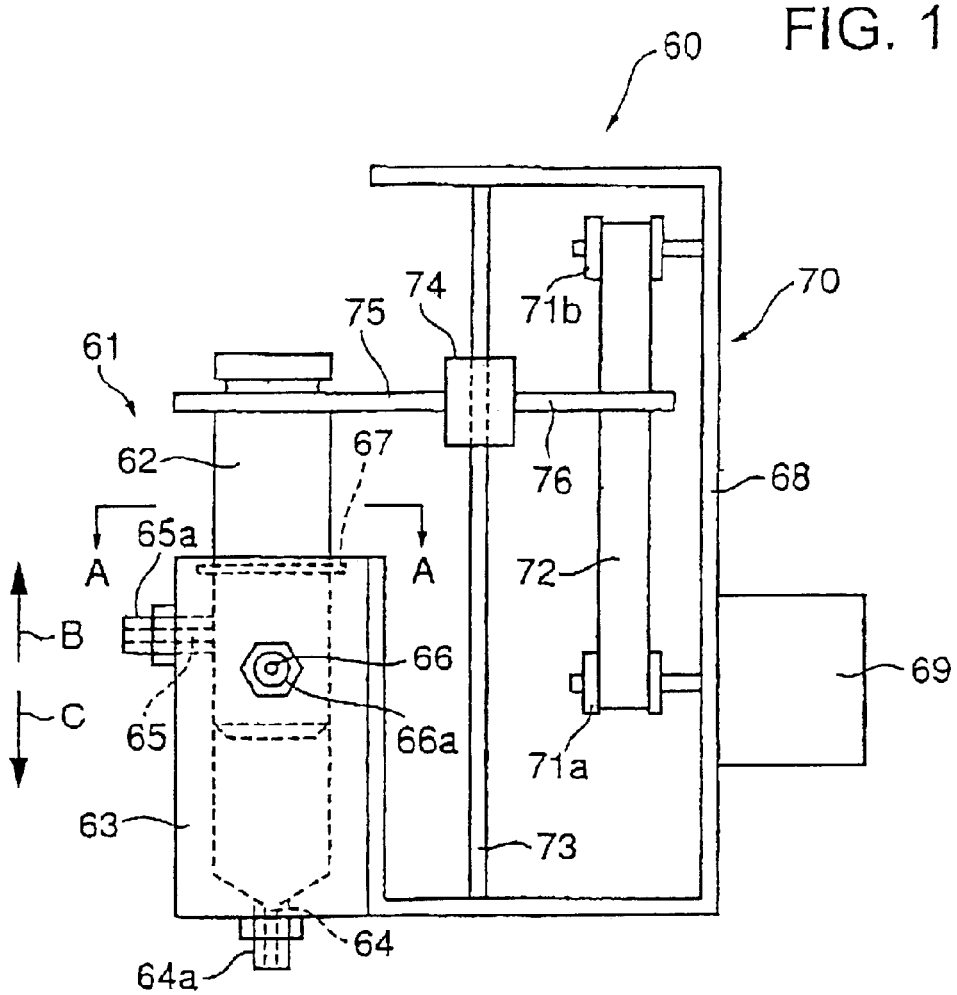
FIG. 1 is a side view showing an embodiment of a sheath liquid supplying apparatus according to the present invention.
Figure 2:
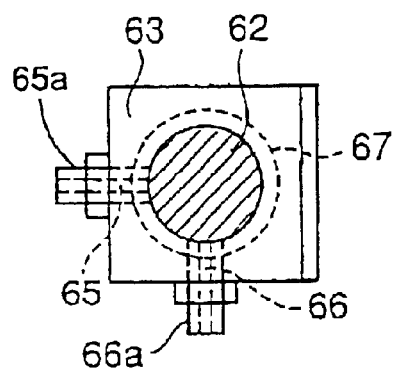
FIG. 2 is a view in section taken along the line A—A in FIG. 1.

FIG. 1 is a side view showing an embodiment of a sheath liquid supplying apparatus according to the present invention and FIG. 2 is a view in section taken along the line A—A in FIG. 1.

As shown in these figures, a main body 60 of a supplying apparatus comprises a syringe 61 and a driving apparatus 70. The syringe 61 has a piston 62 and a cylinder 63 that accommodates the piston 62 so as to be slidable in a direction shown by arrows B and C. The arrow B expresses up direction along the axial direction of the cylinder 63, and the arrow C expresses down direction along the axial direction of the cylinder 63. The piston 62 and cylinder 63 can be made of a material having a chemical resistance, such as glass, vinyl chloride, stainless steel or the like. It is necessary for the syringe 61 to have a capacity, which can at least supply a sheath liquid required for one measurement in a sheath flow cell. For example, the capacity may be approximately 3 to 5 mL.

The cylinder 63 is provided with an injection/suction hole 64 of the sheath liquid at its bottom edge that injects the sheath liquid to the cylinder 63 and extracts the sheath liquid from the cylinder 63 corresponding to the forward and rearward motions of the piston 62. Provided also at the cylinder 63 are a gas introducing hole 65 and a negative pressure introducing hole 66 at its side wall. The gas introducing hole 65 introduces a gas (for example, an air) between a liquid surface of the sheath liquid accommodated in the cylinder 63 and the piston 62 to form a gas layer. A buffer action of the gas layer absorbs a rotational irregularity (periodical fluctuation of a torque), to thereby stabilize the ejecting velocity of the sheath liquid. Accordingly, the gas introducing hole 65 is mounted in the vicinity of a piston inserting opening of the cylinder 63.

A circular seal member 67 is disposed at the upper inside surface of the cylinder 63 for sealing up the inside surface of the cylinder 63 and the outside surface of the piston 62.

The negative pressure introducing, hole 66 is provided closer to the injection/suction hole 64 compared to the gas introducing hole 65 with respect to the axial direction of the cylinder 63. Nipples 64a, 65a and 66a for connecting an external tube are respectively disposed at the injection/suction hole 64, gas introducing hole 65 and negative pressure introducing hole 66 of the syringe 61.

A driving apparatus 70 has a frame 68, a stepping motor 69 mounted to the frame 68, a driving pulley 71a mounted to an output shaft of the stepping motor 69, a follower pulley 71b rotatably supported by the frame 68 and an endless belt 72 bridged between the pulleys 71a and 71b.

The frame 68 has a slide shaft 73 mounted along the axial direction of the cylinder 63 that supports a sliding member 74 so as to be capable of sliding in the direction shown by arrows B and C. The sliding member 74 has arms 75 and 76 which horizontally project to respectively connect to the upper edge of the piston 62 and the endless belt 72.

When the stepping motor 69 rotates, its rotational motion is converted into the linear motion by the pulley 71a, 71b and the endless belt 72. The linear motion is transmitted to-the piston 62 via the arm 76, sliding member 74 and arm 75, whereby the piston 62 can be driven in the directions of B and C.

A motor now on sale can be used as the stepping motor 69. For example, the stepping motor of PK43 AG470-100(12) 6TA-3 manufactured by Sanryu Co., Ltd. can be used as the stepping motor 69 causing the piston 62 to slide in the cylinder 63.

Figure 3:
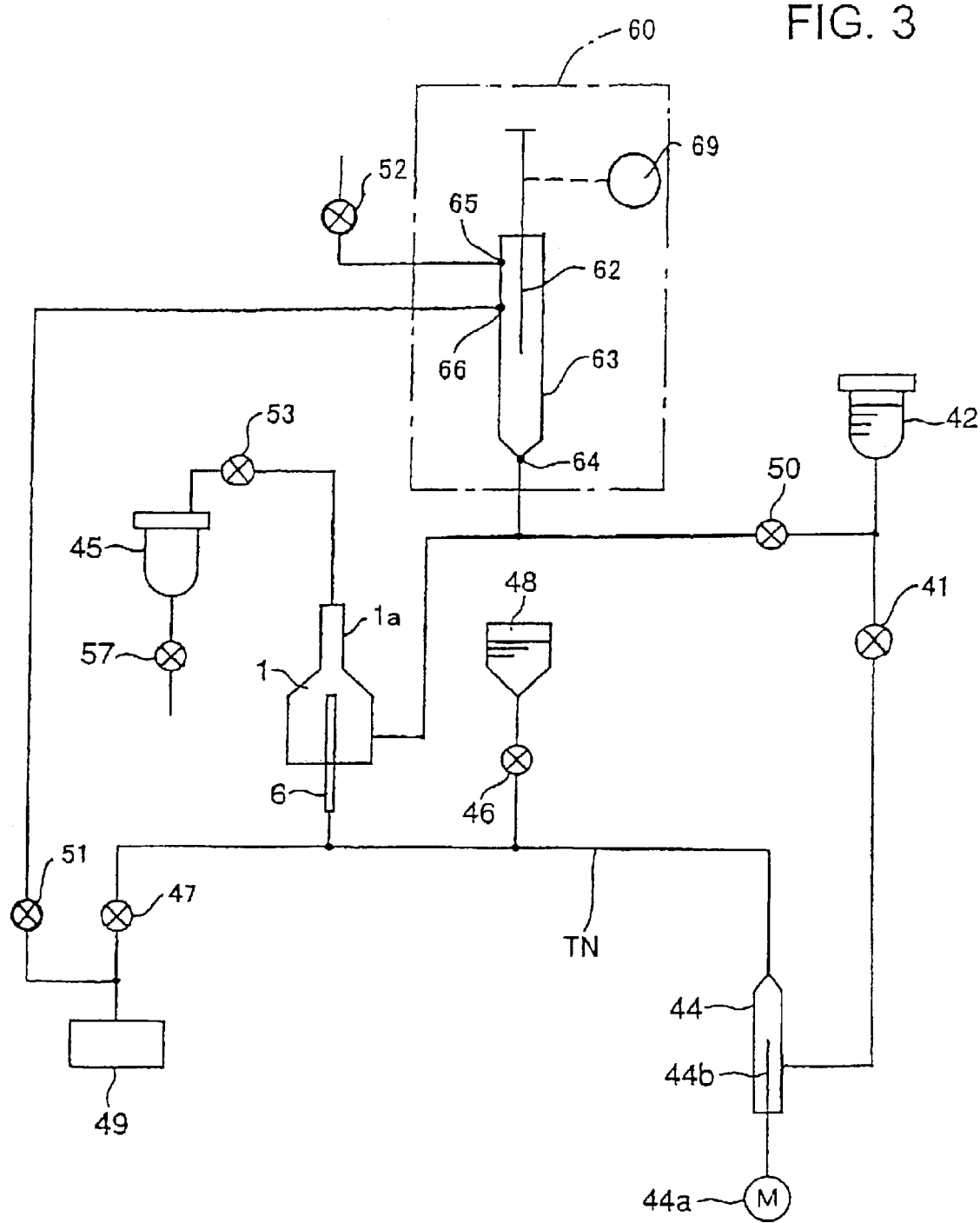
FIG. 3 is a systematic view showing a fluid system of an analyzer of material components in urine that includes the sheath liquid supplying apparatus of the present invention.

Analyzer of Material Components in Urine to which Sheath Liquid Supplying Apparatus is Adapted FIG. 3 is a systematic view showing a flow system where the sheath liquid supplying apparatus in FIG. 1 is adapted to an analyzer of material components in urine. The analyzer is a so-called flow cytometer. Each component of the flow system is connected by flow path of a tube network TN.

Figure 9:
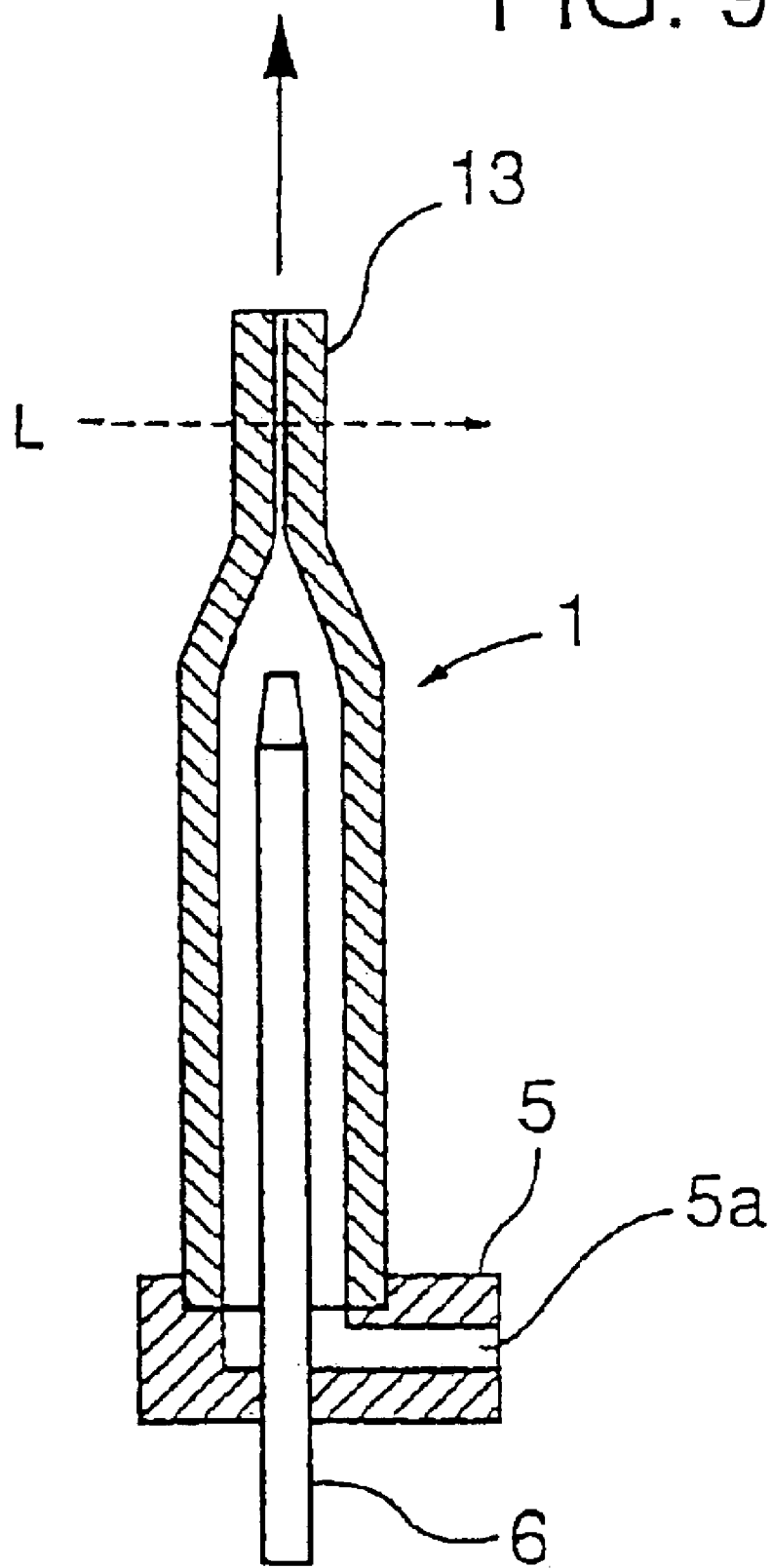
FIG. 9 is a sectional view showing a sheath flow cell of the analyzer of material components in urine to which the sheath liquid supplying apparatus of the present invention is adapted.

A sheath flow cell 1 in this analyzer of material components in urine has a construction shown in FIG. 9. A sheath liquid is supplied from the sheath liquid supplying apparatus 60 to an injection hole Sa of a sheath liquid injecting section 5. A sample liquid is supplied to a nozzle 6 from a syringe 44 for supplying a sample liquid.

Figure 4:
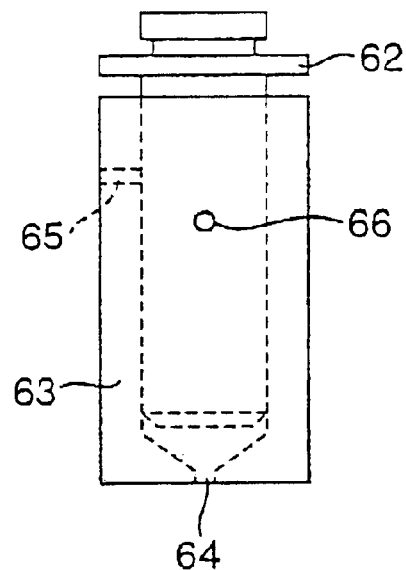
FIG. 4 is an explanatory view showing an operation of a syringe in the embodiment of the present invention.
Figure 5:
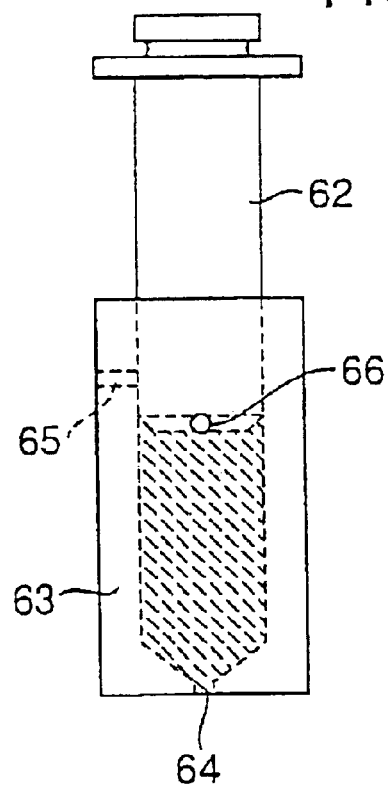
FIG. 5 is an explanatory view showing an operation of a syringe in the embodiment of the present invention.

In an initial condition, the sheath liquid supplying apparatus 60 is in a condition where the leading edge of the piston 62 nearly reaches the injection/suction hole 64 at the bottom of the cylinder 63 as shown in FIG. 4. When a valve 50 is opened to lift the piston 62 in the direction of B (see FIG. 1), the sheath liquid in an open-air sheath liquid chamber 42 is sucked in the cylinder 63 via a valve 50. When the leading edge of the piston 62 reaches the vicinity of the negative pressure introducing hole 66 as shown in FIG. 5, the piston 62 temporarily stops rising, and then, a valve 51 is opened.

By this operation, a negative pressure of a suction apparatus 49 is applied to the inside of the cylinder 63 via the negative pressure introducing hole 66, whereby the sheath liquid is sucked into the suction apparatus 49 via the chamber 42, valve 50, injection/suction hole 64, negative pressure introducing hole 66 and valve 51, so that bubbles are eliminated from the sheath liquid sucked into the cylinder 63.

Subsequently, the valve 51 is closed and the valve 52 is opened, with the result that the piston 62 moves upward until its leading edge passes a little through the gas introducing hole 65. By this operation, air is introduced from the gas introducing hole 65 to thereby form an air layer G (hereinafter referred to as air damper) between the sheath liquid surface and the leading edge of the piston 62.

After the air damper having a predetermined volume is formed, the piston 62 terminates, and the valves 50 and 52 are closed. The sheath liquid supplying apparatus 60 finishes here the preparation for supplying the sheath liquid. A washing process and measuring process are executed as follows.

Washing Process

Firstly, valves 41, 47 and 50 are opened for sucking the sheath liquid with the negative pressure of the suction apparatus 49 from the open-air sheath chamber 42 accommodating the sheath liquid. The sheath liquid is discharged to the suction apparatus 49 via the valve 50, sheath flow cell 1, nozzle 6 and valve 47, and at the same time, discharged to the suction apparatus 49 via a metering syringe 44 for supplying a sample liquid and the valve 47. Thereafter, the valves 41, 47 and 50 are closed after a predetermined period. By this operation, the metering syringe 44, nozzle 6, sheath flow cell 1 and its flow path are washed with the sheath liquid.

Measuring Process

Subsequently, valves 46 and 47 are opened for sucking a sample liquid with the negative pressure of the suction apparatus 49 from a reaction chamber 48 in which a sample liquid containing material components in urine is reacted with a reactant and the resultant is accommodated. When the sheath liquid in the flow path between the valve 46 and the nozzle 6 is replaced with the sample liquid, the valves 46 and 47 are closed.

Figure 7:
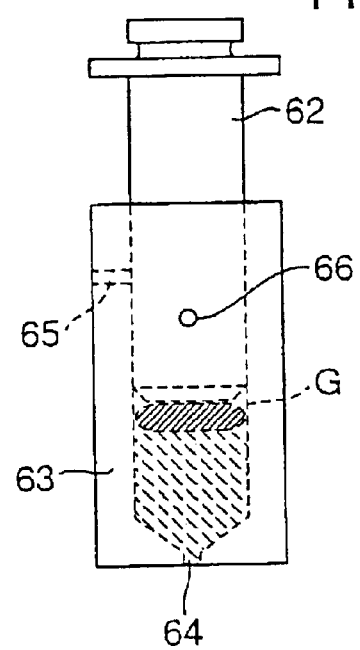
FIG. 7 is an explanatory view showing an operation of a syringe in the embodiment of the present invention.

Next, the valve 53 is opened and the stepping motor 69 of the sheath liquid supplying apparatus 60 is driven for moving the piston 62 toward the injection/suction hole 64 as shown in FIG. 7. By this operation, the sheath liquid in the cylinder 63 is supplied to the sheath flow cell 1 via the injection/suction hole 64, whereby it is injected to the injection hole 5a of the sheath liquid injecting section 5 in the sheath flow cell 1.

Subsequently, a piston 44b of the metering syringe 44 is driven by a motor 44a, whereby the sample liquid present between the valve 46 and the nozzle 6 is ejected from the nozzle 6 as shown in FIG. 9. The ejected sample liquid is converged into a small flow with the sheath liquid for passing through an orifice 13, and then, discharged to an open-air discharge liquid chamber 45 with the sheath liquid.

A laser beam L is irradiated to the orifice portion 13 as described later for optically measuring material components in urine among the sample liquid. Thereafter, the piston 44b of the metering syringe 44 is driven during a predetermined period to supply the predetermined amount of sample liquid to the sheath flow cell 1. Then, the valve 53 is closed to finish the measuring process. The valve 57 is opened, as necessity requires, for discharging the sheath liquid and sample liquid accommodated in the discharge liquid chamber 45.

In the above measuring process, the sheath liquid is pushed by the piston 62 driven by the stepping motor 69 to be supplied from the cylinder 63 to the sheath flow cell 1. The stepping motor originally has a rotational irregularity (periodical fluctuation of torque). This rotational irregularity is absorbed by a buffer operation of the air damper G shown in FIG. 7. As a result, the sheath liquid is smoothly supplied to the sheath flow cell 1 with a constant flow velocity without generating a fluctuation in flow velocity as shown in the result of a performance test described later.

When the measuring process is finished in this way, the process for injecting the sheath liquid to the cylinder 63 of the sheath liquid supplying apparatus 60 and the washing process are performed to make preparations for the next process.

Figure 8:
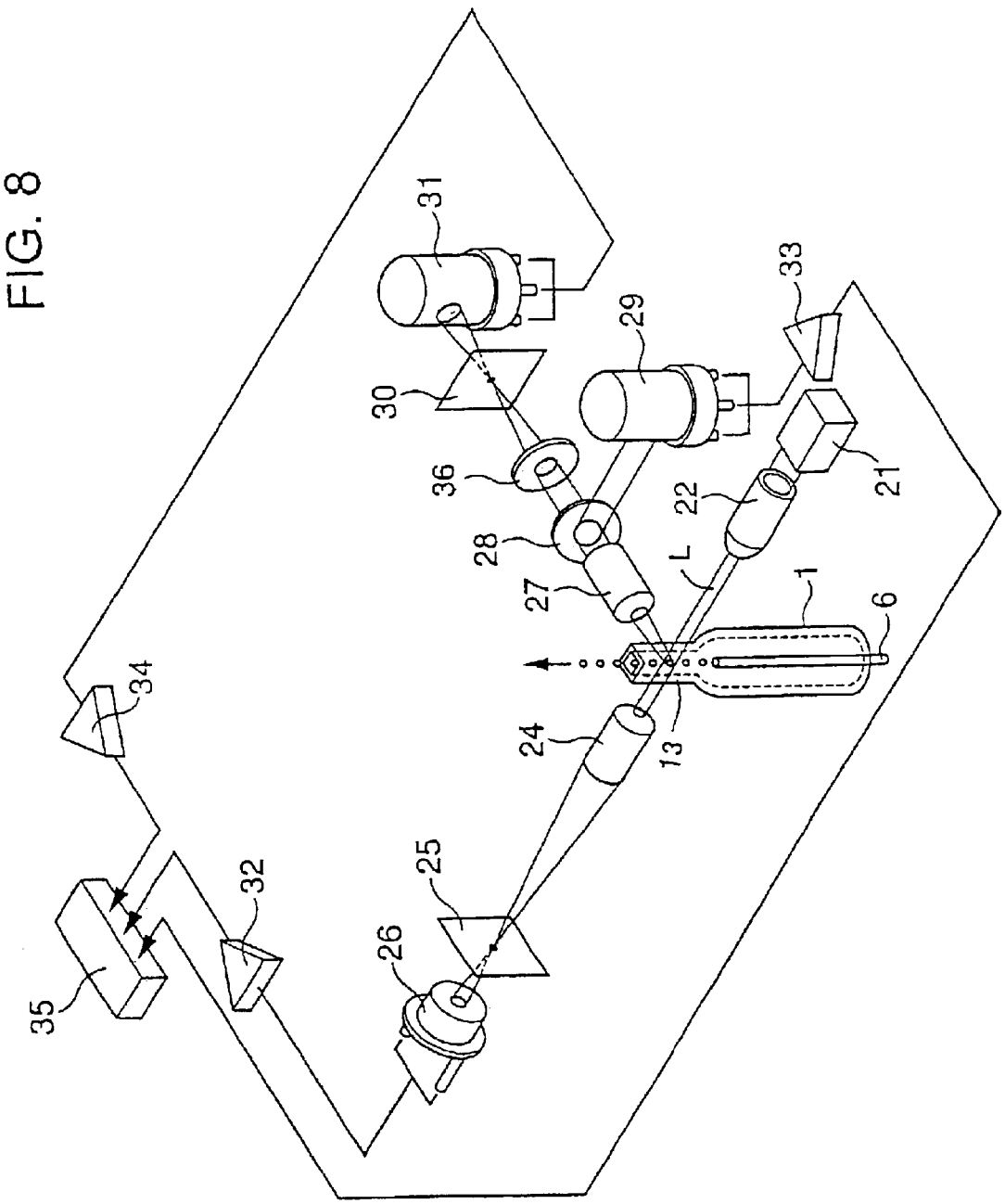
FIG. 8 is a systematic view showing an optical system of an analyzer of material components in urine that includes the sheath liquid supplying apparatus of the present invention.

FIG. 8 is a perspective view showing an optical system of the analyzer of material components in urine. In the same figure, a laser beam L emerged from a laser diode 21 irradiates the orifice portion 13 of the sheath flow cell 1 via a collimator lens 22. The forward scattered light emerging from the material components in urine which pass through the orifice portion 13 is incident to a photodiode 26 via a focusing lens 24 and a pinhole plate 25.

On the other hand, the sideward scattered light emerging from the material components in urine which pass through the orifice portion 13 is incident to a photomultiplier tube (hereinafter referred to as photomul) via a focusing lens 27 and a dichroic mirror 28, while the sideward fluorescence emerging from the material components in urine which pass through the orifice portion 13 is incident to a photomul 31 via the focusing lens 27, dichoric mirror 28, a filter 36 and a pinhole plate 30.

The forward scattered light signal outputted from the photodiode 26, the sideward scattered light signal outputted from the photomul 29 and the sideward fluorescence signal outputted from the photomul 31 are respectively amplified by each amplifier 32, 33 and 34, and then, inputted to an analyzing section 35. The analyzing section 35 is comprised of a microcomputer that processes and analyzes the output signals from the photodiode 26, photomul 29 and 31 based upon a predetermined program and outputs the resultant to a display device or a printer.

Performance Test of Sheath Liquid Supplying Apparatus

A fluctuation in flow velocity (irregularity in flow velocity) of the sheath liquid in the sheath liquid supplying apparatus 60 can be examined by the following manner by using the analyzer of material components in urine shown in FIGS. 3 and 8.

Firstly, a liquid having a refractive index $N_T$ is prepared as a sheath liquid, while a liquid having a refractive index $N_S$ (not equal to $N_T$) is prepared as a sample liquid.

Subsequently, prepared each liquid is supplied to the sheath flow cell 1 by using the flow system shown in FIG. 3. The laser beam L is irradiated to the orifice portion 13 of the sheath flow cell 1 with the optical system of FIG. 8. The photodiode 26 detects its scattered light intensity and the detected light is amplified by the amplifier 32.

The amplified signal waveform is observed by an oscilloscope.

When the ripple occurs in the sample liquid flow at the orifice portion 13 due to the fluctuation in flow velocity of the sheath liquid, the scattered light intensity from the laser beam L changes because of the difference in refractive index between the sheath liquid and the sample liquid flow, whereby the output signal from the amplifier 32 fluctuates (it is considered that the fluctuation in the output signal depends upon "each refractive index of sample liquid and sheath liquid" and "a width of ripple in sample liquid flow").

In view of this, liquids each having the following refractive indices $N_T$ and $N_S$ were prepared as the sheath liquid and sample liquid.

$N_T$=1.341

$N_S$=1.334

Note that liquids each having a different refractive index can be adjusted, for example, with solutions of salt each having a different concentration.

Figure 6:
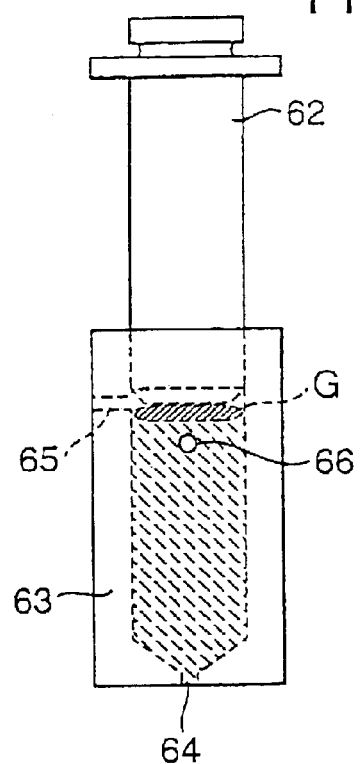
FIG. 6 is an explanatory view showing an operation of a syringe in the embodiment of the present invention.
Figure 10:
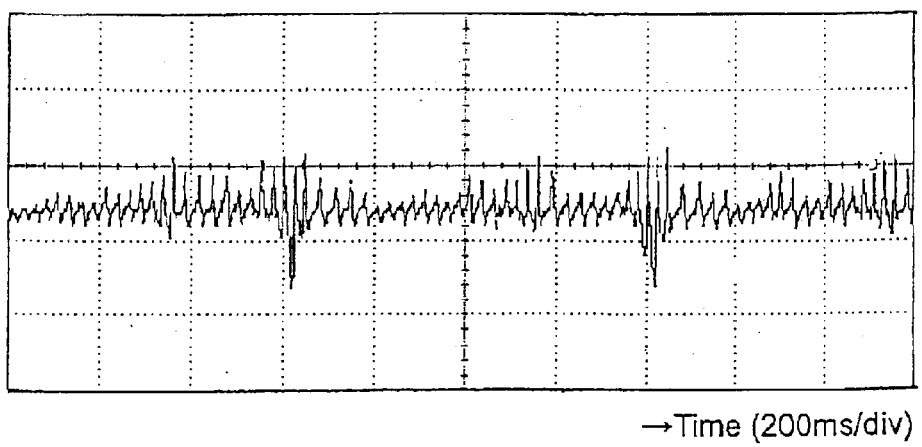
FIG. 10 is a waveform view showing a performance of a comparative example.
Figure 11:
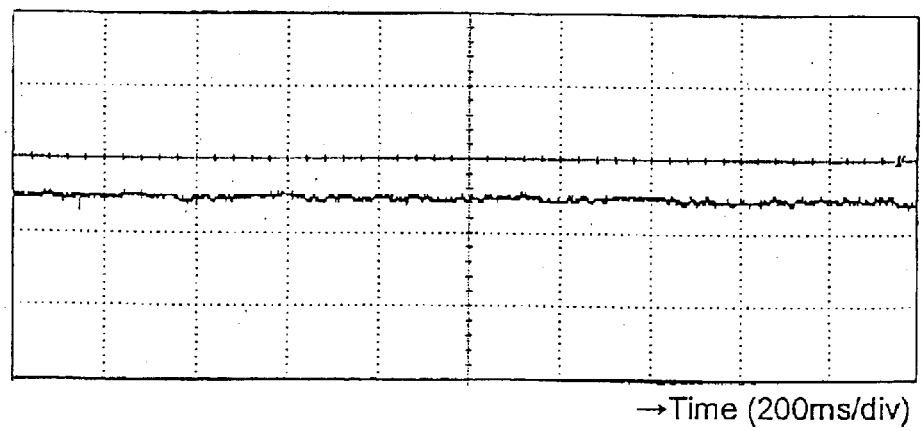
FIG. 11 is a waveform view showing a performance of the embodiment of the present invention.

The flow amount of the sample liquid was set to 1.7 $\mu$L/seconds, while the flow velocity of the sample liquid was set to 7.5 m/seconds that can obtain a laminar flow. The output waveform from the amplifier 32 was recorded with the oscilloscope with respect to the presence of the air damper G (FIGS. 6 and 7). The results are shown in FIGS. 10 and 11. FIG. 10 represents the case where the air damper G is not formed, while FIG. 11 represents the case where the air damper G is formed.

Figure 12:
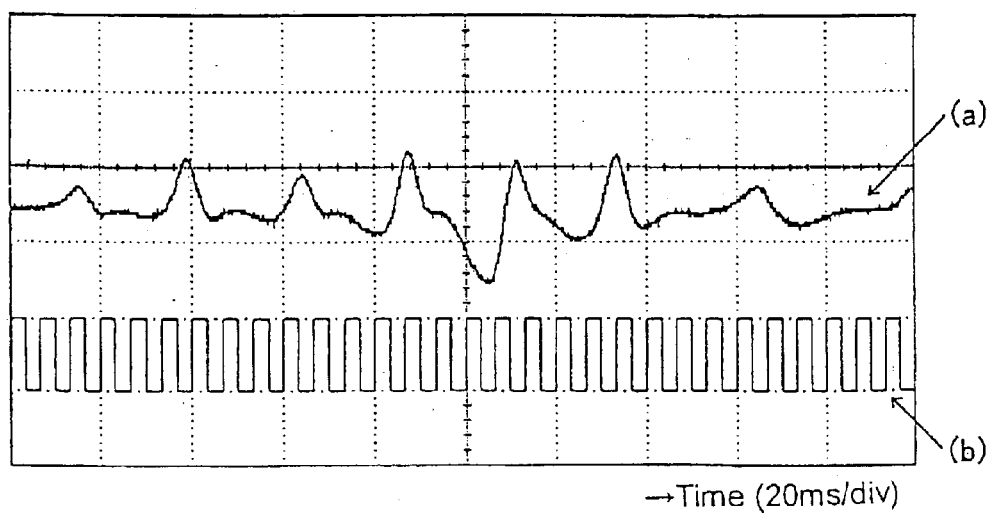
FIG. 12 is an enlarged waveform view showing a performance of the comparative example.

In FIG. 12, a waveform (a) is obtained by recording the waveform in FIG. 10 with a tenfold time axis, while a waveform (b) represents a waveform of a driving pulse of the stepping motor 69 (FIG. 1) corresponding to the waveform (a).

It is understood from FIG. 10 that the waveform has a large fluctuation (ripple) to cause a great ripple in the sample liquid flow at the orifice portion 13 in case where the air damper G is not formed. On the other hand, it is understood from FIG. 11 that the waveform has a small fluctuation to thereby prevent the ripple from occurring in the sample liquid flow in case where the air damper G is formed. Consequently, the formation of the air damper G brings a stable flow of the sample liquid.

FIG. 12 represents that a main cause of the fluctuation in the waveform (a) is caused by the rotational irregularity (periodical fluctuation in torque) of the stepping motor 69 since the correlation is periodically established between the waveform (a) and the waveform (b). FIG. 10 represents that the rotational irregularity is effectively absorbed by the air damper G.

It is understood that the minimum volume necessary for the air damper G may be set to the one that brings a minimum amplitude of the waveform of FIG. 10.

According to a sheath liquid supplying apparatus and its method of the present invention, the supplying apparatus itself can simply be realized with a combination of a syringe and a stepping motor. Further, gas is intervened between a leading edge of a piston in the syringe and a sheath liquid in the cylinder for absorbing a fluctuation of the piston due to the stepping motor, whereby the sheath liquid can be supplied to a sheath flow cell with a constant stable speed.

Moreover, according to an evaluating method of a sheath liquid supplying condition, liquids each having a different refractive index are supplied to a sheath flow cell as a sheath liquid and a sample liquid, and a degree of the fluctuation in the scattered light intensity upon irradiating light to the sheath flow cell teaches information such as a periodical change, fluctuation period, fluctuation width or the like can be obtained with respect to the supplying condition of the sheath liquid. Specifically, it is possible to simplify the evaluating method.

What is claimed is:

1. A sheath liquid supplying apparatus comprising:
   a syringe including a piston and a cylinder slidably accommodating the piston,
   a driving motor for causing the piston to slide in the cylinder,
   wherein the cylinder has a liquid hole for injecting a sheath liquid therethrough out of the cylinder and a gas hole for introducing a gas into the cylinder therehrough.

2. The sheath liquid supplying apparatus claimed in claim 1, wherein the gas hole located relatively above the liquid hole.

3. The sheath liquid supplying apparatus claimed in claim 1, wherein the liquid hole is further used for suction of the sheath liquid into the cylinder therethrough.

4. An apparatus for analyzing particles using the sheath liquid supplying apparatus claimed in claim 1, comprising a measuring section connected to the sheath liquid supplying apparatus,
   wherein the driving motor driving for relatively changing positions of the piston and the cylinder to accommodate the sheath liquid in the cylinder and supply the sheath liquid to the measuring section, with the gas being present in the cylinder.

5. The apparatus of claim 4, further comprising a sample chamber containing a sample liquid therein,
   wherein the sample chamber is connected to the measuring section for supplying the sample liquid to the measuring section, the sheath flow is formed at the measuring section.

6. The apparatus of claim 4, wherein the particles to be analyzed are material components in urine.

7. The apparatus of claim 4, wherein the measuring section has a sheath flow cell, the sheath liquid being supplied from the sheath liquid supplying apparatus to the sheath flow cell.

8. The apparatus of claim 4, wherein the measuring section has an optical detector including a light emitter and a light sensor.

9. The sheath liquid supplying apparatus claimed in claim 1, wherein the driving motor is a stepping motor.

10. A sheath liquid supplying apparatus comprising:
    a syringe including a piston and a cylinder slidably accommodating the piston; and
    a driving motor for causing the piston to slide in the cylinder,
    wherein the cylinder has an injection/suction hole of a sheath liquid positioned at a distal end thereof and a gas introducing hole positioned at a side wall thereof for introducing gas into the cylinder.

11. A sheath liquid supplying apparatus claimed in claim 10, wherein the cylinder has a negative pressure introducing hole positioned at a side wall thereof for introducing a negative pressure into the cylinder.

12. A sheath liquid supplying apparatus claimed in claim 11, wherein the negative pressure introducing hole is positioned closer to the injection/suction hole compared to the gas introducing hole with respect to an axial direction of the cylinder.

13. A sheath liquid supplying apparatus claimed in claim 10, wherein the piston or cylinder is glass, vinyl chloride or stainless steel.

14. A sheath liquid supplying apparatus claimed in claim 10, wherein the syringe has a capacity of about 3–5 mL.

15. A sheath liquid supplying apparatus claimed in claim 10, wherein the driving motor is a stepping motor.

16. A flow cytometer comprising:
    a sheath flow cell;
    a syringe including a cylinder and a piston, said piston and cylinder changeable their relative position to accommodate the sheath liquid therein as well as to supply the sheath liquid to the sheath flow cell therefrom, said syringe provided with a liquid hole for supplying the sheath liquid therethrough to the sheath flow cell and a gas hole for supplying a gas therethrough into the cylinder, said gas hole located relatively above the liquid hole in the syringe; and
    a driving motor for changing the relative position of the piston and the cylinder with the gas being present between the sheath liquid and the piston, whereby the sheath liquid in the syringe is supplied through the liquid hole to the sheath flow cell.

17. The flow cytometer of claim 16, further comprising:
    a sheath liquid chamber containing the sheath liquid therein;
    a tube network connecting said sheath liquid chamber, said syringe and said sheath flow cell for supplying the sheath liquid from the sheath liquid chamber to said syringe and from said syringe to said sheath flow cell.

18. The flow cytometer claimed in claim 17, further comprising a sample chamber containing the sample to the sheath flow cell.

19. The flow cytometer claimed in claim 18, wherein said tube network connecting said sample chamber to said sheath flew cell for supplying the sample from the sample chamber to said sheath flow cell.

20. The flow cytometer claimed in claim 19, further comprising an optical detector including a light emitter and a light sensor.

21. The flow cytometer claimed in claim 20, wherein said sample includes urine and said detector detects material components in urine.

22. An apparatus or analyzing particles using a sheath flow method comprising:
    a measuring section detecting signals from particles;
    a syringe including a piston and a cylinder slidably accommodating the piston, said piston and cylinder being changeable in their relative position to accommodate the sheath liquid therein and supply the sheath liquid to the measuring section, said cylinder having a liquid hole for injecting a sheath liquid therethrough and a gas hole for introducing a gas therethrough into the cylinder;
    a driving motor for relatively changing positions of the piston and the cylinder with the gas being present in the cylinder, whereby the sheath liquid in the syringe is supplied through the liquid hole to the measuring section for forming the sheath flow.

23. The apparatus of claim 22, further comprising a sample chamber containing a sample liquid therein,
   wherein the sample chamber is connected to the measuring section for supplying the sample liquid form the sample chamber to the measuring section for forming the sheath flow.

24. The apparatus of claim 22, wherein the particles are material components in urine.

25. The apparatus of claim 22, wherein the measuring section has a sheath flow cell, the sheath liquid being supplied from the sheath liquid supplying apparatus to the sheath flow cell.

26. The apparatus of claim 22, wherein the measuring section has an optical detector including a light emitter and a light sensor.

27. The apparatus of claim 22, wherein the driving motor is stepping motor.

* * * * *